United States Patent [19]

Okada

[11] Patent Number: 5,002,042
[45] Date of Patent: Mar. 26, 1991

[54] ENDOSCOPE APPARATUS PROVIDED WITH A TIP ATTACHMENT LOOSENING CONFIRMING FUNCTION

[75] Inventor: Minoru Okada, Sagamihara, Japan

[73] Assignee: Olympus Optical Co., Ltd., Tokyo, Japan

[21] Appl. No.: 344,864

[22] Filed: Apr. 28, 1989

[30] Foreign Application Priority Data

Jul. 6, 1988 [JP] Japan .................. 63-90124[U]

[51] Int. Cl.⁵ .............................. A61B 1/06
[52] U.S. Cl. ........................................ 128/6
[58] Field of Search ........................... 128/4–7

[56] References Cited

U.S. PATENT DOCUMENTS

| | | | |
|---|---|---|---|
| 4,085,742 | 0/1978 | Okada | 128/4 |
| 4,219,013 | 0/1980 | Okada | 128/6 |
| 4,620,769 | 0/1986 | Tsuno | 128/6 |
| 4,676,230 | 6/1987 | Miyazaki . | |
| 4,706,653 | 0/1987 | Yamamoto | 128/4 |
| 4,765,313 | 0/1988 | Kumakura | 128/4 |
| 4,794,911 | 0/1989 | Okada | 128/4 |
| 4,856,495 | 0/1989 | Tohjoh et al. | 128/6 |
| 4,860,732 | 0/1989 | Hasegawa et al. | 128/6 |

FOREIGN PATENT DOCUMENTS

| | | | |
|---|---|---|---|
| 2533004 | of 1976 | Fed. Rep. of Germany | 128/6 |
| 57-87704 | 5/1982 | Japan . | |
| 0040415 | of 1987 | Japan | 128/4 |
| 63-234935 | 9/1988 | Japan . | |

Primary Examiner—Benjamin Layno
Attorney, Agent, or Firm—Armstrong, Nikaido, Marmelstein, Kubovcik & Murray

[57] ABSTRACT

A tip attachment provided with a mount fittable to a mount receptacle in the tip part of an endoscope is made to appear within the visual field of an observing optical system provided in the tip part before the tip attachment comes to separate from a predetermined fitted state so that the tip attachment may be prevented in advance from dropping.

23 Claims, 9 Drawing Sheets

ENDOSCOPE APPARATUS PROVIDED WITH A TIP ATTACHMENT LOOSENING CONFIRMING FUNCTION

BACKGROUND OF THE INVENTION

Field of the Invention and Related Art Statement

This invention relates to an endoscope apparatus wherein an attachment such as a hood fitted to the tip of the endoscope can be prevented from falling off.

Recently, endoscopes have come to be extensively used in the medical field and industrial field.

Figure 1:
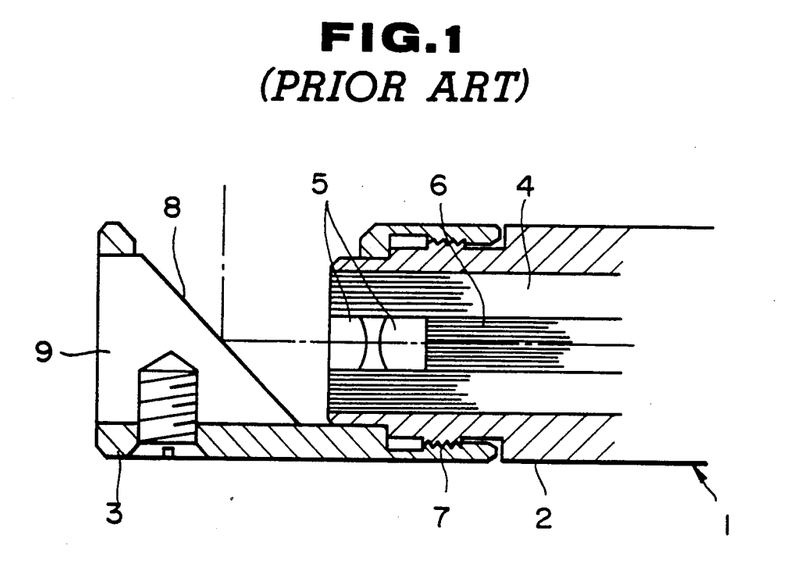
FIG. 1 is a sectioned view showing the tip side of an endoscope fitted with an optical adapter in a prior art example.

There is a prior art example in which the above mentioned endoscopes can be fitted with an optical adapter 3 which can change the visual field direction in the tip (formation) part 2 of the endoscope bodY 1 as shown in FIG. 1 so that a proper observation in response to an object may be made.

The above mentioned endoscope 1 is provided with an illuminating optical system by a light guide 4 transmitting an illuminating light and emitting it from the tip surface, an objective optical system 5 and an observing optical system having the entrance end surface of an image guide 6 as an image transmitting means arranged in the image forming position of this objective optical system 5.

The above mentioned tip part 2 is provided on the outer peripheral surface with a screw part 7 so that a side viewing optical adapter 3 may be in order that a side view may be observed. This optical adapter 3 is fitted with a prism 9 provided with a reflecting surface 8.

In case the above mentioned optical adapter 3 is not fitted, a hood will be fitted.

Figure 2:
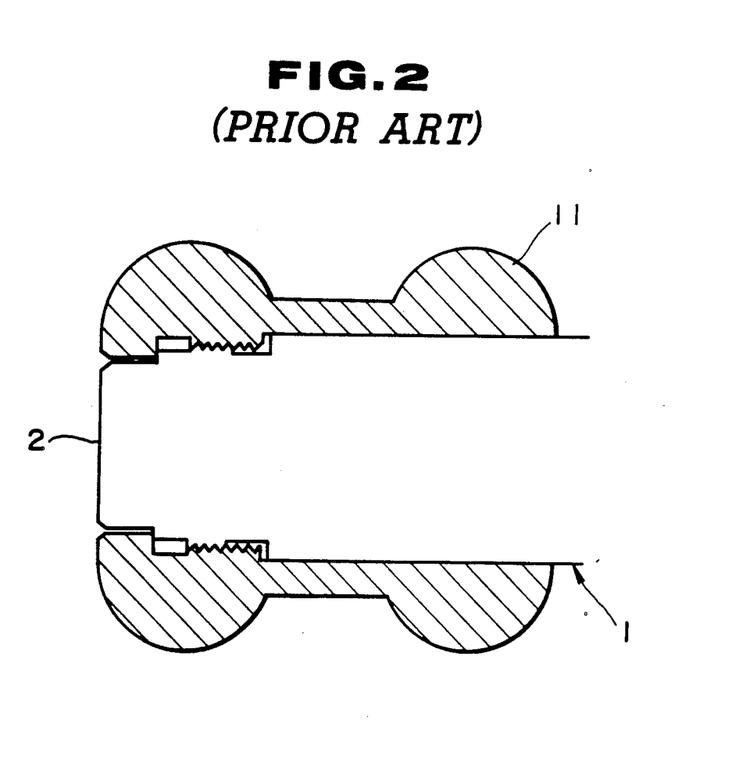
FIG. 2 is a sectioned view showing a centering device fitted to an endoscope tip.

Also, the endoscope body 1 may be fitted in the tip part 2 with a gourd-shaped centering device 11 as shown in FIG. 2 so that the observing position may be set near the center axis of a pipe or the like and it may be easy to observe the inner peripheral surface of the pipe. In case the centering device 11 is not fitted, a hood will be fitted.

Known as a means of preventing the above mentioned removably fitted member from dropping is a Japanese Utility Model Application Laid Open No. 87704/1982.

This relates to an optical adapter or hood having windows coinciding respectively with an observing optical system and illuminating optical system within an endoscope body. This optical adapter or hood requires a positioning means for the endoscope body and is complicated in the structure.

Figure 3A:
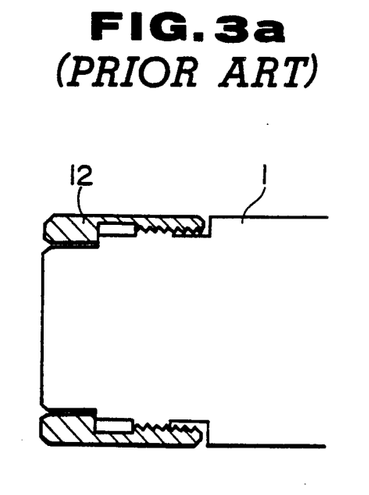
FIGS. 3a and 3b are explanatory views showing a hood respectively as fitted to and separated from an endoscope tip.

On the other hand, there is also an endoscope to which is connected a substantially hollow cylindrical hood of a non-conductive material for electric insulation or a substantially hollow cylindrical hood 12 prerequisited to be removed to be repaired as is described in a Japanese Patent Application No. 26512/1987 (See FIG. 3a).

Such a hood is bonded and fixed to the endoscope body but has a danger that, when it is exposed to a high temperature by mistake during inspection, the bonding strength is reduced by the variation with the lapse of time and a vibration or shock is applied to the tip part of the endoscope, the connection will loosen and the hood will fall off.

The endoscope connected with such a substantially hollow cylindrical member has so far no means of warning the inspector in advance of the loosening of the connection.

Figure 3B:
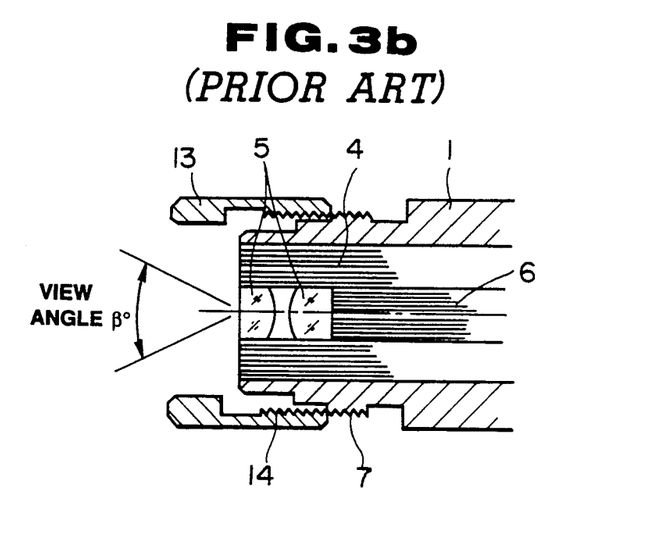

That is to say, as shown in FIG. 3b, even when the screwed engagement of the female screw part 14 of the substantially hollow cylindrical member 13 of a hood or the like with the male screw part 7 of the endoscope body 1 is released, the observing visual field of a view angle $\beta$ will not be disturbed by the substantially hollow cylindrical member 13.

In the means shown in the Japanese Utility Model Application Laid Open No. 87704/1982, as a window requiring positioning for the observing optical system and illuminating optical system is formed, there are defects that the structure is complicated and a work of a high precision is required.

Also, in the endoscope in which the substantially hollow cylindrical member is connected to the tip part, as the observing visual field of the endoscope will not be disturbed even at the time when the substantially hollow cylindrical member is separated from the endoscope body as shown in FIG. 3b, even if the connection of the substantially hollow cylindrical member loosens during the endoscope inspection, the inspector will not be able to recognize it. If the inspection is continued as it is, the substantially hollow cylindrical member will drop and a serious accident will follow. Thus, there have been defects that essentially unnecessary disassembling and recovering operations will be necessary and a time loss and high cost will be caused.

An endoscope provided with a removable inserting guide is disclosed in U.S. Pat. No. 4,676,230.

This prior art example is so made that the inserting guide may not drop from the tip of the insertion part. This structure is comparatively simple but is considerably more complicated than the above described devices in FIGS. 1 to 3.

OBJECTS AND SUMMARY OF THE INVENTION

An object of the present invention is to provide an endoscope apparatus wherein, with a very simple structure, a tip attachment removably fitted to the tip part can be prevented from dropping.

Another object of the present invention is to provide an endoscope apparatus high in safety.

A further object of the present invention is to provide an endoscope apparatus which can warn the user of the occurrence of the possibility of dropping before the attachment drops.

In the present invention, a visual field varying mechanism is provided so that a tip attachment provided with a mount engaging with a mount receptacle in an endoscope tip part will partly enter the visual field of an observing means of the endoscope at least before it separates from the predetermined fitted state and therefore the tip attachment ;can be recognized before it separates.

BRIEF DESCRIPTION OF THE DRAWINGS

FIGS. 4 to 8 relate to the first embodiment of the present invention.

FIGS. 13 to 15 relate to the fourth embodiment of the present invention.

FIGS. 17 to 20 relate to the sixth embodiment of the present invention.

DETAILED DESCRIPTION OF THE PREFERRED EMBODIMENTS

Figure 6:
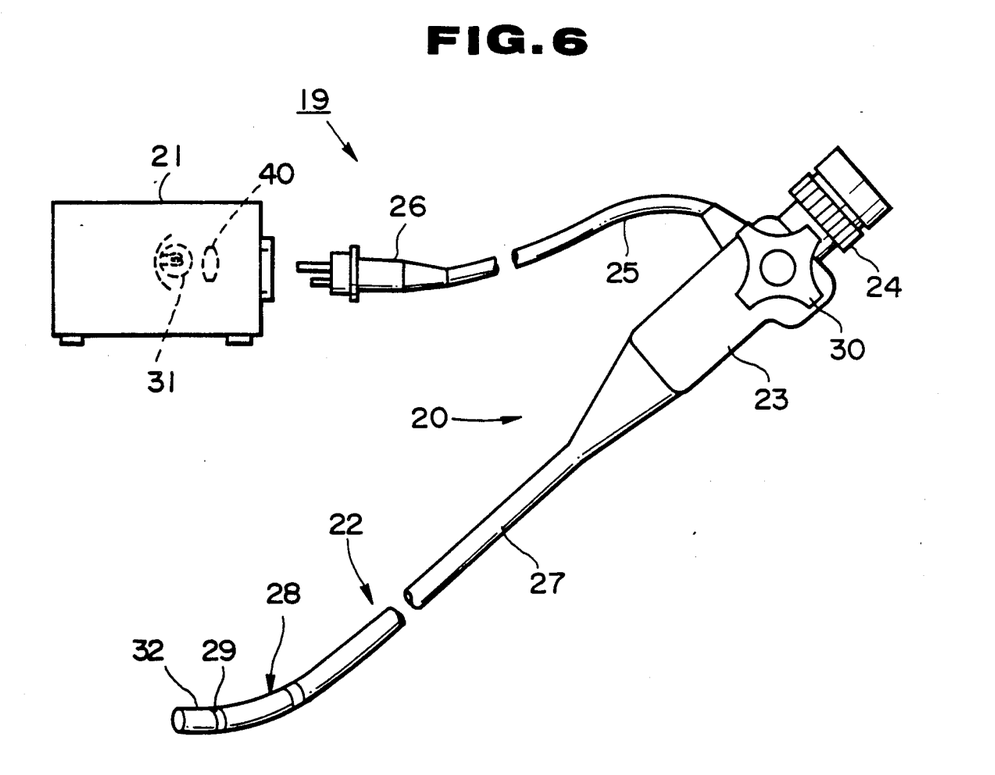
FIG. 6 is a general appearance view showing the first embodiment.

As shown in FIG. 6, an endoscope apparatus 19 of the first embodiment comprises an optical endoscope 20 and a light source unit 21 feeding an illuminating light to this endoscope 20. This endoscope 20 is formed of an elongate insertable part 22, an operating part 23 provided at the rear end of this insertable part 22, an eyepiece part 24 provided at the rear end of this operating part and a light guide cable 25 extended out of the side of the above mentioned operating part 23.

A connector 26 which can be removably fitted to the light source unit 21 is fitted to the end of the above mentioned light guide cable 25.

The above mentioned insertable part 22 is formed of a flexible part 27 formed of a flexible material, a curvable part 28 formed at the front end of this flexible part 27 and a rigid tip forming part 29 formed at the front end of this curvable part 28. This curvable part 28 can be curved vertically and horizontally by rotating an angle knob 30 provided in the operating part 23.

A lamp 31 outputting a white light is contained within the light source unit 21 so that, when the connector 26 is fitted, an illuminating light will be condensed by a condenser lens 40 and will be fed to the light guide end surface at the end of the light guide cable 25.

Figure 4:
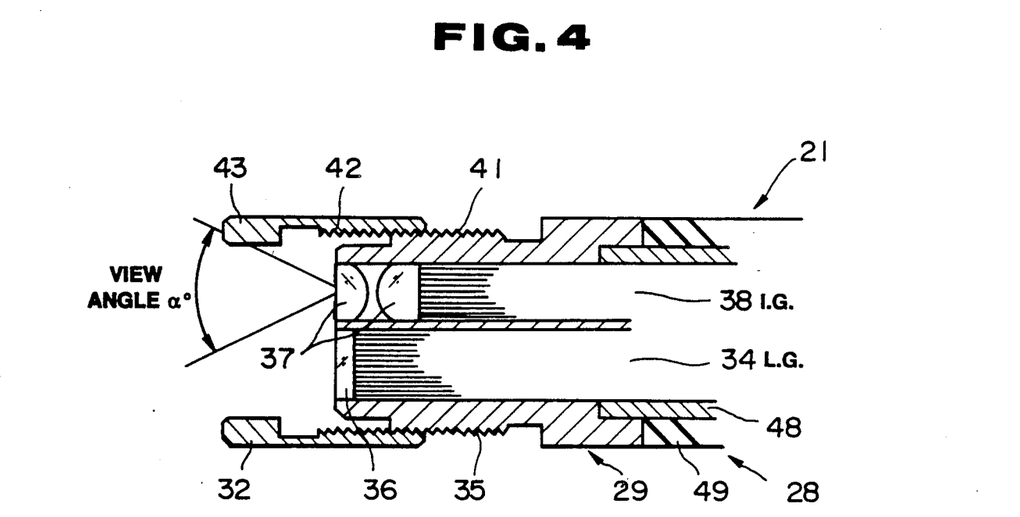
FIG. 4 is a sectioned view showing the tip side of the first embodiment as the fitting of a hood has loosened.
Figure 5:
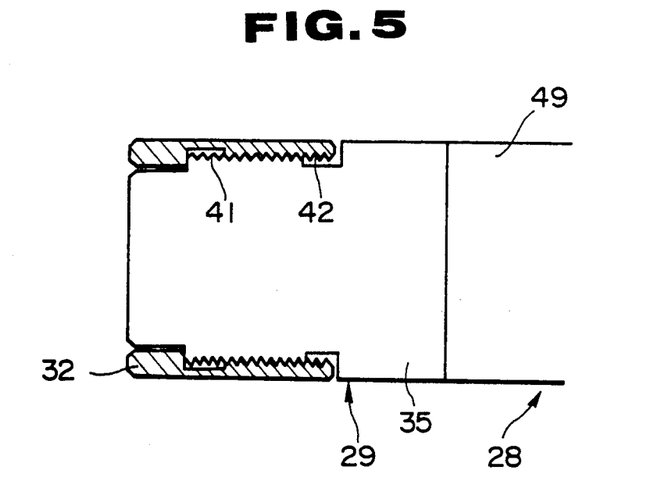
FIG. 5 is a sectioned view showing a hood as normally fitted.

Now, the endoscope body or, in this case, the tip forming part 29 can be fitted with a substantially hollow cylindrical hood 32 shown in FIG. 4 or 5.

This hood is to protect a later described male screw 41 in case a centering member 33 or the like is not used.

Figure 7:
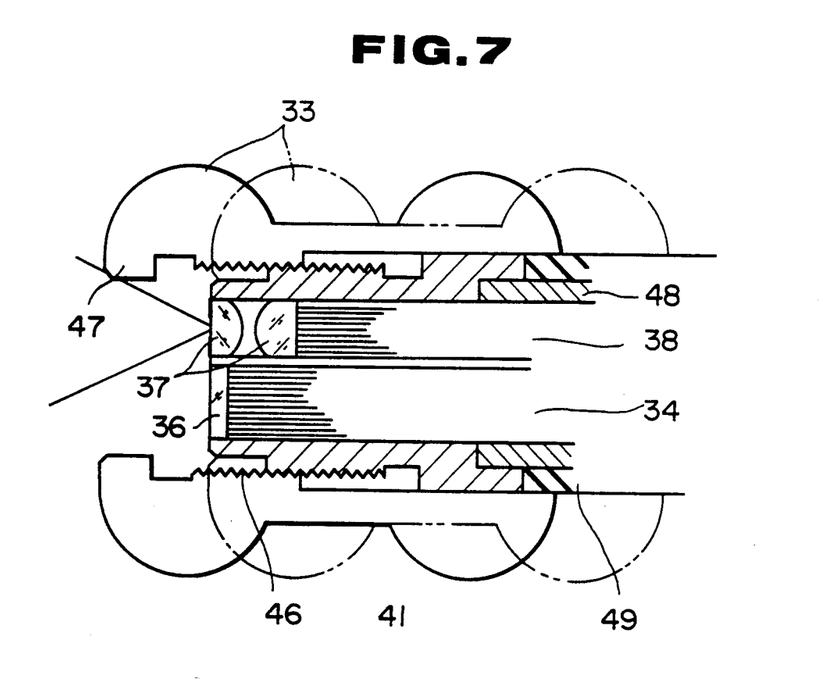
FIG. 7 is a sectioned view showing the tip side of the first embodiment as fitted with a centering member.

Also, in case the above mentioned hood 32 is removed, a centering device member 33 as is shown in FIG. 7 will be able to be fitted to be used or an optical adapter 3 as is shown in FIG. 1 will be able to be fitted.

The above mentioned centering device member 33 is to be used in the case of being inserted into a part (such as within a plant in the industrial field) considerably thicker than the insertable part 22 so as to dissolve that the insertable part will be eccentric and only a part of a pipe wall will be able to be observed.

Within the above mentioned insertable part 22, as shown in FIG. 4, a light guide 34 transmitting an illuminating light is inserted, is secured at the tip within a through hole of a tip member 35 forming the tip forming part 29 and is fitted on the tip surface (exit end surface) with a cover glass 36 so that the illuminating light may be emitted forward from the illuminating window fitted with this cover glass 36 to illuminate an object part or the like.

A through hole is provided adjacently to the above mentioned illuminating window to form an observing window to which an objective optical system 37 is secured and an image guide 38 is secured on the tip side so that the tip surface of the image guide 38 transmitting an optical image may be present in the position of the focal plane of this objective optical system 37 to form an observing optical system.

The above mentioned image guide 38 transmits an optical image to the eyepiece part 24 side so as to be observable through an eyepiece lens (not illustrated) arranged as opposed to the exit end surface of this image guide 38.

Figure 8:
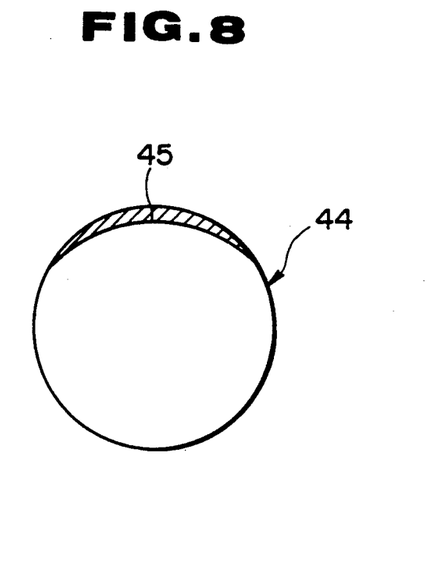
FIG. 8 is an explanatory view showing that in case the fitting of a hood has loosened, it will appear as a warning index within the observing visual field.

Now, the above mentioned tip part member 35 is smaller in the outside diameter as stepped on the front side and has a male screw 41, which is over half as long as the stepped part, to be a mount receiving means formed on the outer peripheral surface so that a hood 32, in which a female screw 42 to be screwed with this male screw 41, may be fitted. This hood 32 as correctly fitted in the predetermined fitted state is as shown in FIG. 5 but, when the screwing of both screws 41 and 42 loosens as shown in FIG. 4 from this predetermined fitted state, a projection 43 projecting radially inward will enter an observing visual field 44 of a view angle α and, as shown in FIG. 8, the above mentioned projection 43 will appear as a warning index 45.

Also, as shown in FIG. 7, in case a centering member 33 is fitted, when the female screw 46 of this centering member 33 loosens from the normal fitted state indicated by the two-point chain lines to the position indicated by the solid lines, the projection 47 will appear as a warning index within the visual field to warn the user that the centering member 33 is close to dropping. A tip frame 48 forming the curvable part 28 is secured to the rear end of the tip member 35 and frames (not illustrated) are, connected in tandem in the rear of this tip frame 48. The curvable part 28 is covered on the outer periphery with a flexible tube 49.

The operation by the thus formed first embodiment shall be explained in the following.

As shown in FIG. 5 or 4, the hood 32 is used as fitted in the normal fitted state, is exposed to a high temperature during the inspection and is subjected to a vibration, shock and the like on the tip side to be loosened in the fitting. When the hood is continued to be used as thus loosened, the loosening will progress to be as shown in FIG. 4. In this state, the projection 43 of the hood 32 will enter the view angle of the observing visual field 44 and will appear as a warning index 45 as shown in FIG. 8. In the case of this state, the inspector will be able to recognize it with the observation from the eyepiece part 24, will interrupt the inspection, will pull out the endoscope 20, will re-set it in the normal fitted state and may use it again. In case the loosening is thus produced, it will appear as the warning index 45 and therefore the hood 32 will be able to be prevented in advance from dropping.

Also, in case the centering member 33 is fitted and used instead of the hood 32, even if a loosening is produced from the normal fitted state indicated by the two-point chain lines in FIG. 7, when the loosening progresses, for example, to the position indicated by the solid lines, the same as in the case of the hood 32, the warning index will appear within the observing visual field and therefore the dropping will be able to be prevented in advance. Such a substantially hollow cylindrical member as the hood 32 is not required to be positioned in the rotating direction for the tip member 35, is simple in the fitting (connecting and bonding) structure and therefore can be made low in the cost.

In the case that the optical adapter 3 shown in FIG. 1 is fitted, as different from the case of the objective optical system 5 of the endoscope 1 of the prior art example shown in FIG. 1, as the optical axis of the objective optical system 37 is greatly deflected from the center axis of the tip member 35, if only a small loosening is produced, the light distributing characteristics will greatly vary, a part of the observing visual field will be intercepted and the loosening will be able to be known from this.

The hood 32 is formed to be long at the tip and is projected forward at the tip as fitted to the insertable part so as to prevent the object from being too close to the observing window to be observed.

Figure 9:
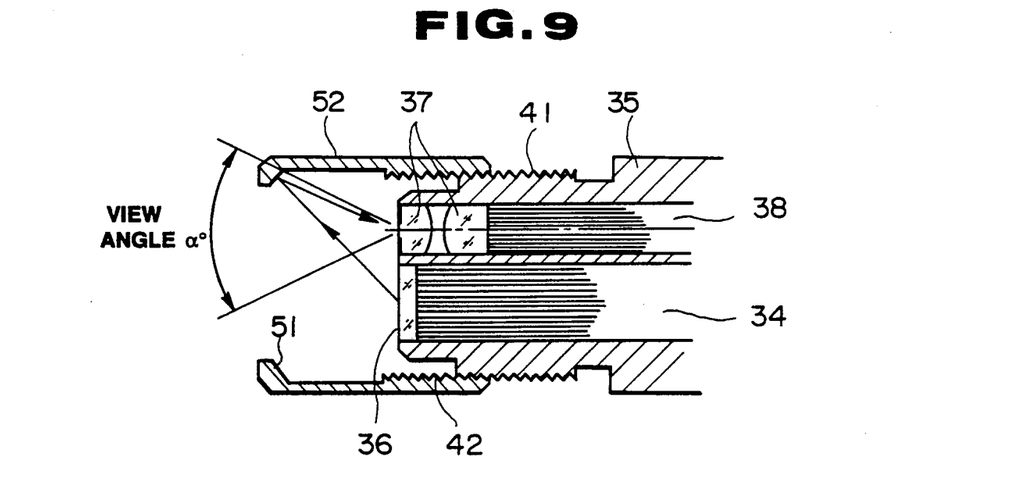
FIG. 9 is a sectioned view showing the tip side in the second embodiment of the present invention.

FIG. 9 shows the tip side of the second embodiment of the present invention.

Figure 10:
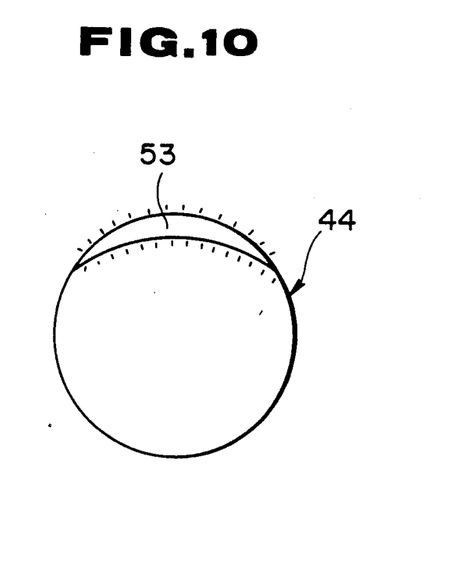
FIG. 10 is an explanatory view showing an observing visual field in the case of FIG. 9.

In the second embodiment, a hood 52 provided with a reflecting part 51 is fitted instead of the hood 32 of the first embodiment. That is to say, the substantially cylindrical hood 52 is provided with the female screw 42 the same as in the first embodiment and can be set in the normal fitted state by screwing the female screw 42 with the male screw 41. Also, this hood 52 is provided on the inner periphery at the front end with a reflecting part 51 plated or the like with a material of a high reflection factor so that, as shown in FIG. 9, when the fitting loosens, the illuminating light emitted through the cover glass 36 will be reflected by the reflecting part 51, will enter the observing visual field 44 and will appear as a warning index by a bright line 53 as shown in FIG. 10.

The other formations are the same as in the first embodiment and have substantially the same operations and effects.

Figure 11:
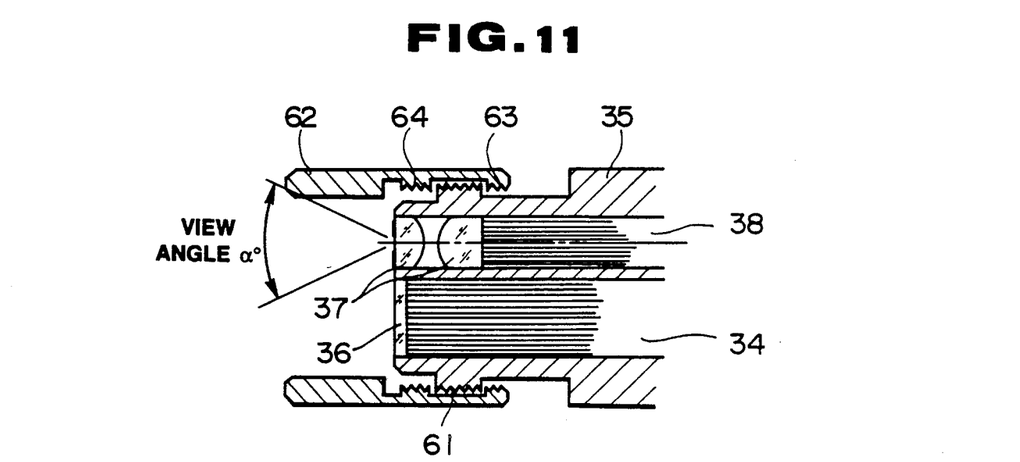
FIG. 11 is a sectioned view showing the tip side in case the fitting has loosened in the third embodiment of the present invention.
Figure 12:
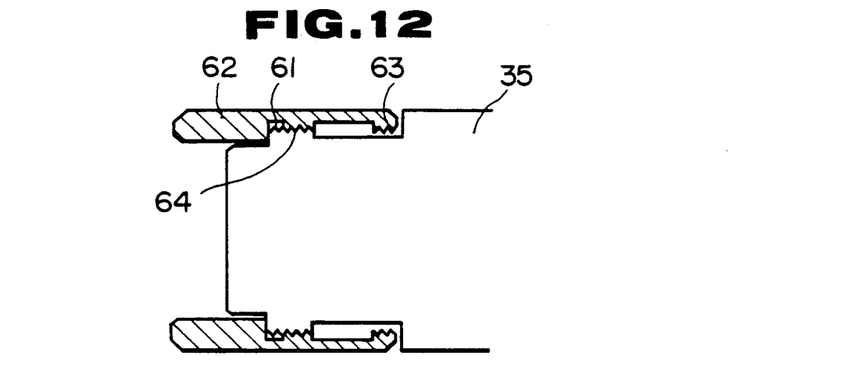
FIG. 12 is a sectioned view showing the tip side as normally fitted.

FIGS. 11 and 12 show essential parts of the third embodiment of the present invention.

In this third embodiment, the tip member 35 is provided with a male screw 61 shorter than in the first embodiment. A hood 62 fitted to this tip member 35 is provided with a first female screw 63 and second female screw 64 as separated in the lengthwise direction. This separating distance is made larger than the width of the male screw 61 so that, in case the screwing of the second female screw 64 with the male screw 61 is released as shown in FIG. 11, the male screw 61 will be able to be set as screwed with neither of both female screws 63 and 64. In the state shown in FIG. 11, the tip side of the hood 62 will appear as a warning index within the visual field (for example, in FIG. 8).

According to this third embodiment, when a loosening is produced from the normal fitted state as shown in FIG. 12 and the screwing of the second female screw 64 is released, the first female screw 63 will be set as not screwed with the male screw 61 as shown in FIG. 11. Therefore, unless the first female screw 63 is screwed with the male screw 61 again and further loosening progresses, no drop will occur. Also, in the state shown in FIG. 11, the tip side of the hood 62 will enter the observing visual field and a warning index will appear as in the first embodiment.

Therefore, in the case of the state shown in FIG. 11, when a warning index appears, if the inspection is interrupted and the loosening is corrected, the danger of causing a drop will be able to be made less than in the first embodiment. That is to say, when the first female screw 63 and male screw 61 are screwed with each other in the position relation in the rotating direction, a drop will be caused from the state shown in FIG. 11. However, the probability of causing such a screwed engagement is so small that the danger of dropping can be made small enough by this safe design.

The other formations, operations and effects are the same as in the first embodiment.

In FIG. 12, a second male screw may be provided so as to be screwed with the first female screw 63.

Figure 13:
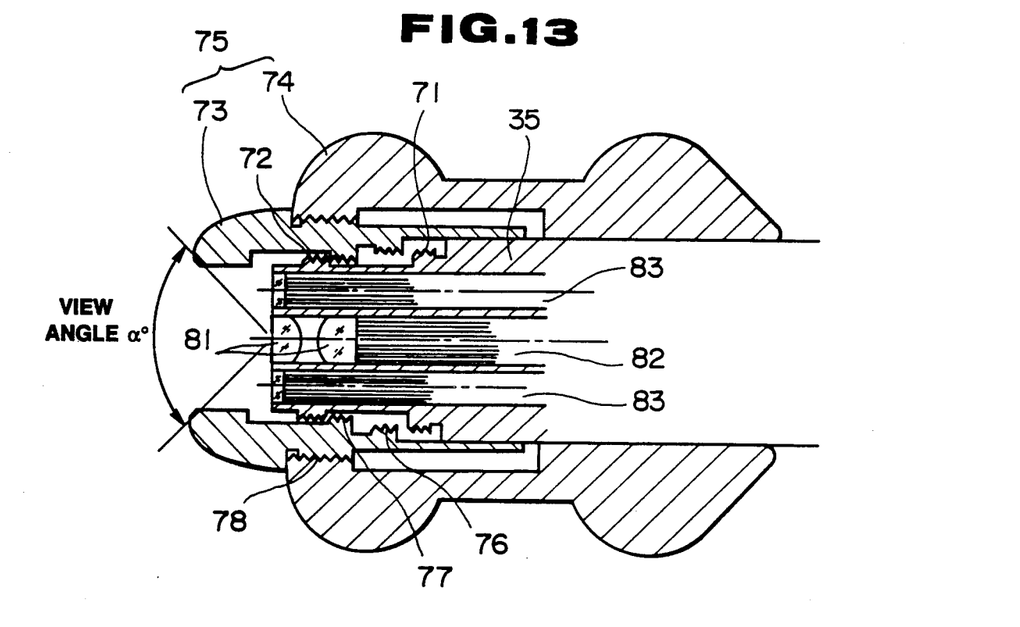
FIG. 13 is a sectioned view of the tip side as the fitting of the centering device has loosened.
Figure 14:
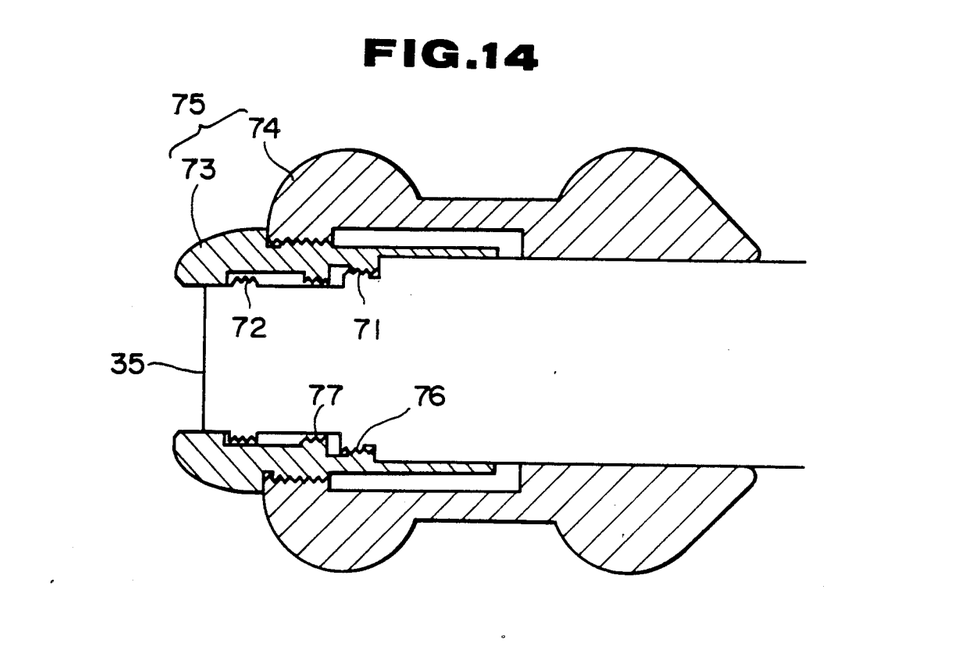
FIG. 14 is a sectioned view showing a centering device as normally fitted.

FIGS. 13 and 14 show essential parts of the fourth embodiment of the present invention.

The tip member 35 to be an endoscope body in this embodiment is provided on the outer peripheral parts of different diameters with a first male screw 71 and second male screw 72 as separated from each other. This tip member 35 is to be fitted with a centering device 75 consisting of a substantially hollow cylindrical member 73 and a diameter changing member 74.

The above mentioned substantially hollow cylindrical member 73 is provided on the inner peripheral surface with a first female screw 76 and a second female screw 77 screwable respectively with the above mentioned first male screw 71 and second male screw 72 as separated from each other. Also, this substantially hollow cylindrical member 73 is provided on the outer peripheral surface with a male screw 78 to be screwed with a female screw of the diameter changing member 74 having a gourd-shaped contour to be replaceably fitted. When the diameter changing member 74 different in the largest outside diameter part is replaced and fitted, the centering device 75 will have a function of being able to be positioned on the center axis of a pipe to be inspected.

The distance between the first male screw 71 and second male screw 72 is made longer than both ends of the first female screw 76 and second female screw 77 so as to have a size covering them inside. Also, in the normal fitted state, as shown in FIG. 14, it is so set that the first female screw 76 may be screwed with the first male screw 71. As shown in FIG. 13, the tip of the substantially hollow cylindrical member 73 is made to enter the observing visual field.

In this embodiment, an objective optical system 81 is provided so that its optical axis may coincide substantially with the center axis of the tip member 35, an image guide 82 is arranged so that its entrance end surface may be present in the image forming position of the objective optical system 81 and a light guide 83 is provided on the periphery (or in two places) of this objective optical system 81.

According to the thus formed fourth embodiment, the centering device 75 as correctly fitted is as shown in FIG. 14. When the fitting loosens from this state and the screwed engagement of the first male screw 71 with the first female screw 76 is released, they will be as shown in FIG. 13. In the state shown in FIG. 13, the tip side of the substantially hollow cylindrical member 73 will enter the observing visual field and the inspector will be able to know that the fitting has loosened.

If a drop preventing means is applied in the state shown in FIG. 13, as the actual drop from this state can not occur unless after the screwing again of the second male screw 72 with the female screw 77, even if the measures are taken after the warning index is indicated, the danger of the drop will be able to be substantially positively prevented.

Figure 15:
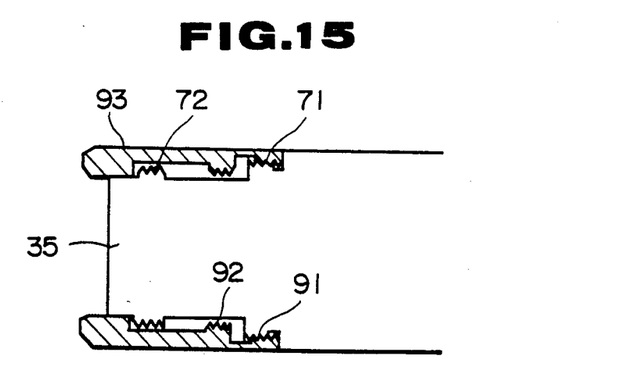
FIG. 15 is a sectioned view showing a hood as normally fitted.

In case the above mentioned centering device 75 is not used, the same as the substantially hollow cylindrical member 73, as shown in FIG. 15, a substantially cylindrical hood 93 provided with a first female screw 91 and second female screw 92 will be able to be fitted. Also, without using this hood 93, the substantially cylindrical member 73 as not fitted with the diameter changing member 74 can be fitted and used.

Figure 16:
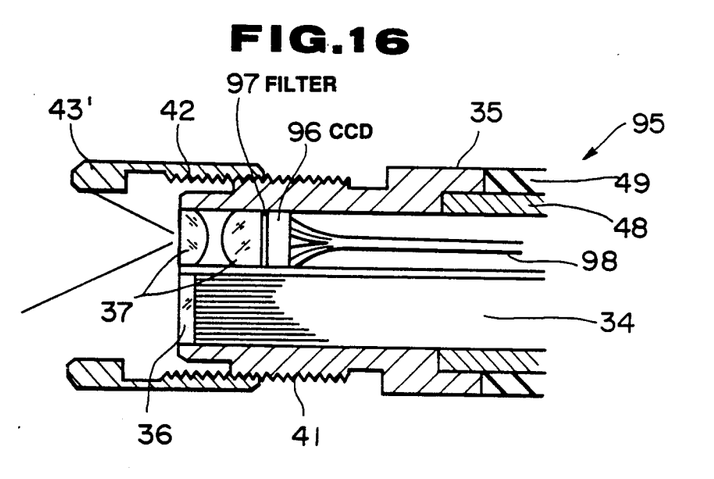
FIG. 16 is a sectioned view showing a hood in the fifth embodiment of the present invention as loosened in the fitting.

The above described respective embodiments have been explained on the optical endoscope but, as shown in FIG. 16, can be applied also to an electronic endoscope 95.

Figure 17:
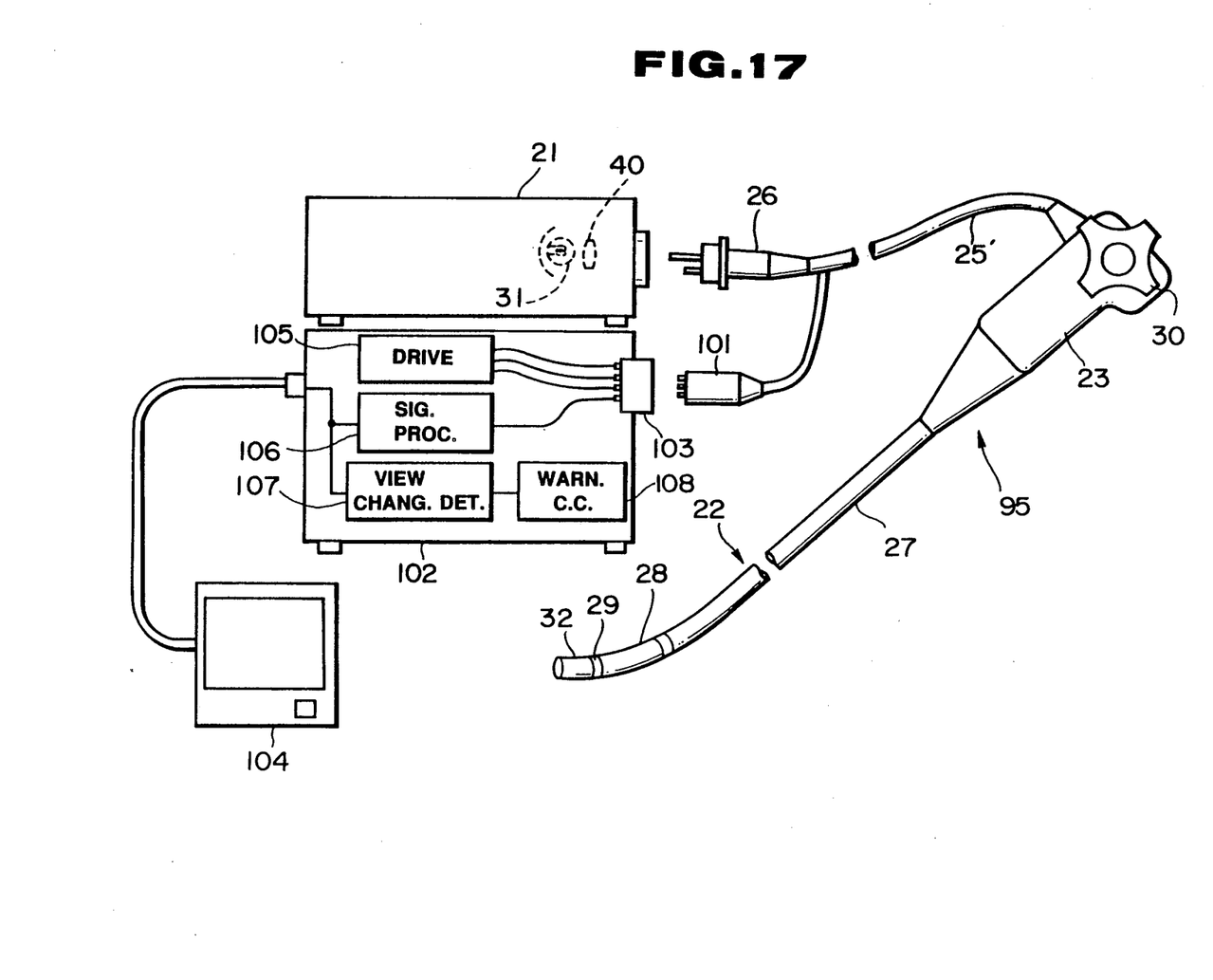
FIG. 17 is a general formation view.

The above mentioned electronic endoscope 95 is of an appearance shown in FIG. 17 and is of a contour having no eyepiece part 23 in the endoscope 20 shown in FIG. 6. A universal cord 25' is extended instead of the light guide cable 25 out of the operating part 23. A light guide connector 26 and signal connector 101 fitted to the tips of this cord 25' can be fitted respectively to the light source unit 21 and a connector receptacle 103 of a signal processing apparatus 102. By this signal processing apparatus 102, the signal is processed to produce a standard video signal which can be displayed on a monitor 104.

In the above mentioned electronic endoscope 95, a CCD 96 having an optical converting function is arranged in the focal plane of the objective optical system shown in FIG. 16. A color separating mosaic filter 97 is fitted in front of the imaging surface of this CCD 96 to separate colors for each pixel. A signal cable 98 is connected at one end to the CCD 96 and leads at the other end to the signal connector 101. The others are fundamentally of the same structure as of the optical endoscope 20 and the same reference numerals are attached respectively to the same members.

In the above mentioned electronic endoscope 95, when the connector 101 is connected to the signal processing apparatus 102, the CCD 95 and signal processing apparatus 102 will be electrically connected with each other through the signal cable 98. When a CCD driving signal is applied to the CCD 95 from a driving circuit 105 within the signal processing apparatus 102, an electric charge signal photoelectrically converted by this CCD 96 will be read out and will be input into the signal processing circuit 106. By this signal processing circuit 106, the signal is converted to three-primary color signals, for example, of an NTSC system and is color-displayed by a monitor 104.

Figure 18:
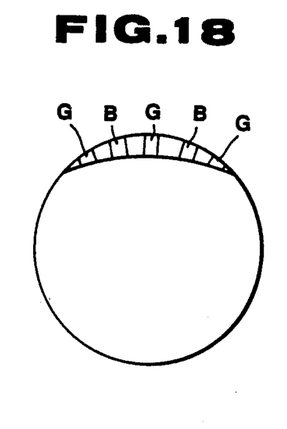
FIG. 18 is an explanatory view showing visual field variations as caused.

This signal processing circuit 106 is connected with the visual field variation detecting circuit 107 so that, when the projection 43' enters the visual field of the imaging optical system, for example, as shown in FIG. 18, the visual field variation detecting circuit 107 will operate to operate a warning circuit 108.

In order to make it easy to detect that the projection 43' has entered the visual field, for example, as shown in FIG. 18, green and blue stripe-like colored parts are formed so that, in case a part of the green and blue stripes is detected, the warning circuit 108 will warn the user.

Figure 19:
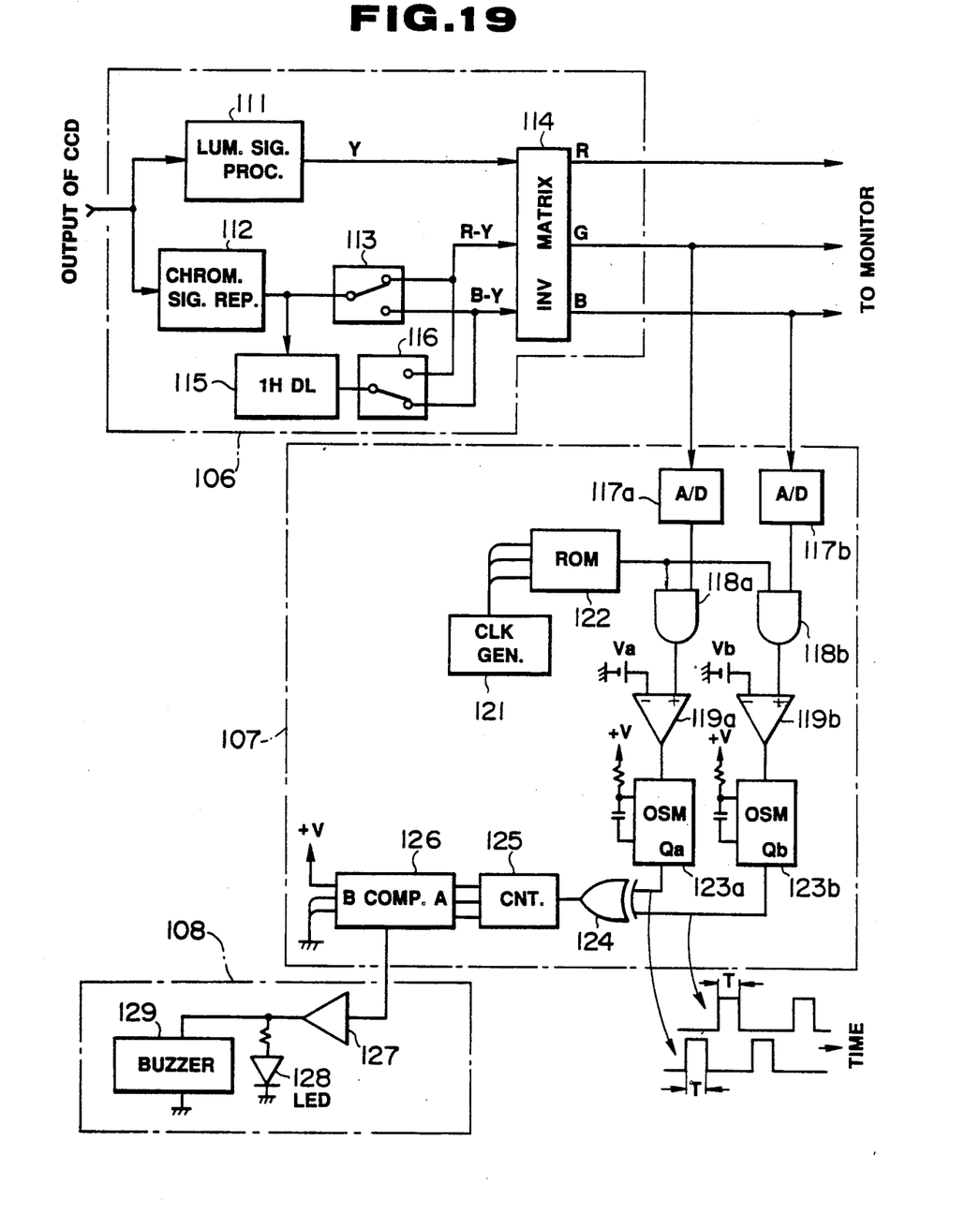
FIG. 19 is a circuit diagram showing examples of a signal processing circuit and visual field variation detecting circuit.

The formations of the above mentioned signal processing circuit 106 and visual field variation detecting circuit 107 are shown in FIG. 19.

A luminance signal Y is produced through a luminance signal processing circuit 111 from an output signal of the CCD 96 and is also input into a chromatic signal reproducing circuit 112 and color difference signals R-Y and B-Y are produced in time series on each horizontal line, are input into an inverted matrix circuit 114 through an analog switch 113 and are input into the inverted matrix circuit 114 through a delay deviCe 115 giving a delay amount of lH (one horizontal period) and an analog switch 116.

The above mentioned two analog switches 113 and 116 are switched alternately as operatively connected in each lH period and synchronized color difference signals R-Y and B-Y are output.

The luminance signal Y and color difference signals R-Y and B-Y are input into the above mentioned inverted matrix circuit 114 and the three primary color signals R, G and B are output and are input into a monitor 104.

For example, the green and blue signals G and B are converted to digital signals respectively through A/D converters 117a and 117b and are input into comparing circuits 119a and 119b respectively through AND gates 118a and 118b.

Figure 20A:
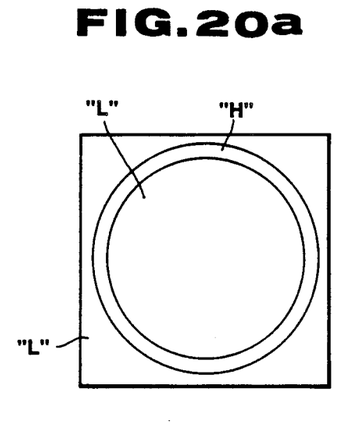
FIG. 20 shows explanatory views showing signal parts passed through data and AND gate within a ROM.

The above mentioned AND gates 118a and 118b are controlled to open and close by the output of a ROM 122 read out by a clock of a clock generator 121. In this case, as shown in FIG. 20a, two-valued data is written into this ROM 122 so as to open only in the ring-like part. The (large) circle outside this ring-like part corresponds to the size of the visual field on the monitor picture surface. The inside (small) circle is somewhat smaller than the outside circle and, in the case of FIG. 18, as in FIG. 20b, a part of it will be input into the comparing circuits 119a and 119b through the gates.

The outputs of the above mentioned AND gates 118a and 118b are compared respectively with fixed levels Va and Vb in the comparing circuits 119a and 119b. By these comparisons, as in the case of FIG. 20b, when green and blue stripes appear within the visual field, the outputs of the comparing circuits 119a and 119b will become "H". The outputs of the above mentioned comparing circuits 119a and 119b are input respectively into one-shot multivibrators (abbreviated as OSM hereinafter) 123a and 123b and, when an "H" signal is applied to a trigger input end, a pulse of a fixed pulse width T will be output. This pulse width T is set to correspond to the width of the stripe.

An exclusive logical sum of the outputs of the above mentioned OSM 123a and 123b is taken through an exclusive OR circuit 124. That is to say, as the stripes of green and blue are not simultaneously detected, the case that the green and blue signals are simultaneously detected is excluded.

The output of the above mentioned exclusive OR (abbreviated as EX-OR hereinafter) circuit 124 is input into a counter 125, the number of times of the detection of green and blue of the stripes is counted, the output of the counter 125 is input into a digital comparator on one side and a preset value is input on the other side.

When a signal of a counted number larger than the preset value is input into this comparator 126, an "H" output will be output to the warning circuit 108 and an LED 128 and buzzer 129 will be operated through a driver 127.

According to this embodiment, when the stripes of the projection 43' enter the visual field, the stripes will be detected and will automatically warn the user through the warning circuit 108.

Figure 20B:
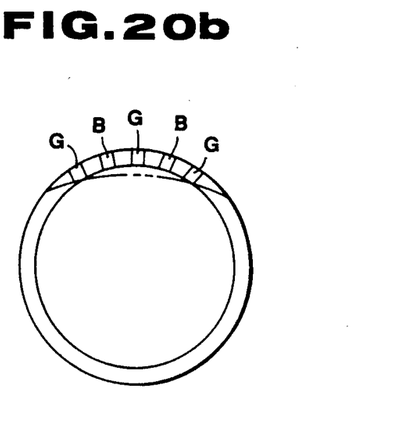

In this embodiment, the visual field variation is detected by hardware but can be also detected, for example, by comparing the state in FIG. 20b with a preset pattern by software.

Even if a television camera is fitted to the eyepiece part of an optical endoscope, this embodiment will be able to be used in the same manner.

The detection of the visual field variation is not limited to the one in which stripes are formed.

Also, it is apparent that the present invention can be applied in the same manner even to the case of a frame sequential type color imaging system.

Another embodiment can be also formed by partly combining the above described respective embodiments.

What is claimed is:

1. An endoscope apparatus comprising:
    an elongate insertable part;
    an observing optical system arranged on a tip front surface of said elongate insertable part; and
    a substantially hollow cylindrical shaped tip attachment having a female screw part to be screwed with a male screw part, provided on an outer periphery of said elongate insertable part tip, and fitted to said elongate insertable part tip,
    wherein a length of screwed engagement of said male screw part and female screw part with each other is made long enough for at least a part of said tip attachment to enter an observing visual field before said tip attachment is separated from the elongate insertable part.

2. An endoscope apparatus according to claim 1 wherein said tip attachment is a hood for protecting said male screw part.

3. An endoscope apparatus according to claim 1 wherein said tip attachment is a centering device supporting the elongated insertable part substantially in a center within a tube in which it is inserted.

4. An endoscope apparatus according to claim 1 wherein said tip attachment has on a tip side inside surface a reflecting part reflecting endoscope illuminating light.

5. An endoscope apparatus according to claim 1 wherein a length of said male screw part in an axial direction of said male screw part extends more than half a length of a distal end of said elongate insertable part, and a moving distance in the axial direction, for engaging said substantially hollow cylindrical shaped tip attachment when the tip attachment is attached, is longer than a distal end length of said elongate insertable part.

6. An endoscope apparatus comprising:
    an elongate insertable part;
    an observing optical system arranged on a tip front surface of said elongate insertable part and having an observing visual field directed forward;
    a substantially hollow cylindrical shaped tip attachment to be fitted to said elongate insertable part tip;
    a first screw connecting means arranged between said insertable tip part and said tip attachment and connecting both with each other; and
    a second screw connecting means arranged between said insertable part tip and said tip attachment and connecting both with each other after said first screw connecting means loosens and releases the connection,
    wherein at least part of said tip attachment enters the visual field of said observing optical system before connection by said second screw connecting means.

7. An endoscope apparatus according to claim 6 wherein a length of said first screw connecting means in an axial direction of said first screw connecting means extends more than half a length of a distal end of said elongate insertable part, and a moving distance in the axial direction, for engaging said tip attachment when the tip attachment is attached, is longer than a distal end length of said elongate insertable part.

8. An endoscope apparatus comprising:
    an elongate insertable part;
    an observing means provided on a front surface of a distal end of said elongate insertable part;
    a tip attachment having openings at front and rear ends and a cylindrical space within the tip attachment;
    a male screw means provided on an outer periphery at the distal end of said elongate insertable part; and
    a female screw means provided on an inner periphery of the tip attachment;
    wherein a length of screwed engagement of said male screw means and female screw means with each other is made long enough for at least a tip of said tip attachment to be placed within an observing visual field of said observing means at an engagement starting position and to be placed on a proximal end side beyond the observing visual field at an engagement completing position.

9. An endoscope apparatus according to claim 8 wherein said tip attachment is a substantially cylindrical hood.

10. An endoscope apparatus according to claim 8 wherein said tip attachment is a centering device provided with a large diameter part projecting in a radial direction and variable in size of an outside diameter when fitted to a tip part of said elongate insertable part.

11. An endoscope apparatus according to claim 8 wherein at least one of said male screw means and female screw means is provided as separated in two places.

12. An endoscope apparatus according to claim 9 wherein, a reflecting part provided on the inner periphery of the front end of said tip attachment will appear within the visual field before the screwed engagement is released.

13. An endoscope apparatus according to claim 8 wherein, a colored part provided on the inner periphery of the front end of said tip attachment will appear within the visual field before the screwed engagement is released.

14. An endoscope apparatus according to claim 8 further having a signal processing means to produce a standard video signal and a monitor means displaying said video signal.

15. An endoscope apparatus according to claim 14 further having a detecting circuit and a warning means issuing a warning with an output signal of said detecting circuit.

16. An endoscope apparatus according to claim 8 wherein said observing means makes the observing visual field deviate from an axis of the elongate insertable part in order to assist the tip of the tip attachment to enter the observing visual field at the engagement starting position of said male and female screw means.

17. An endoscope apparatus according to claim 8 wherein said observing means includes an imaging device and an optical device guiding light of a predetermined observing visual field to said imaging device.

18. An endoscope apparatus according to claim 8 wherein a length of said male screw means in an axial direction of said male screw means extends more than half a length of a distal end of said elongate insertable part, and a moving distance in the axial distance, for engaging a tip attachment when the tip attachment is attached, is longer than a distal end length of said elongate insertable part.

19. An endoscope apparatus comprising:
an elongate insertable part;
an observing means provided on a front surface of a distal end of said elongate insertable part; and
a male screw means provided on an outer periphery at the distal end of said elongate insertable part,
wherein a length of said male screw means in an axial direction of said male screw means extends more than half a diameter of the distal end of said elongate insertable part, and a moving distance in the axial direction, for engaging a tip, attachment when the tip attachment is attached, is longer than half a diameter of said elongate insertable part.

20. An endoscope apparatus comprising:
an elongate insertable part;
an observing means provided on a front surface of a distal end of said insertable part;
a tip attachment having openings at front and rear ends and a cylindrical space within the tip attachment; and
a connecting means for strengthening an extent of connection with movement of said tip attachment in a distal end direction and axial direction provided on a touching surface between an outer periphery surface at the distal end of said insertable part and an inner periphery surface of said tip attachment,
wherein a tip part of said tip attachment is placed on a border of an observing visual field of said observing means when the tip attachment comes to a predetermined position between a connecting starting position and connecting completing position.

21. An endoscope apparatus according to claim 20 wherein said tip attachment includes a projected part projecting inside a direction of a radius at the tip part of said tip attachment.

22. An endoscope apparatus according to claim 20 wherein said connecting means consists of a male screw means provided on an outer periphery at the distal end of insertable part and a female screw means provided on an inner periphery of the tip attachment.

23. An endoscope apparatus according to claim 22, wherein at least one of said male screw means and female screw means is divided into two screw parts arranged in the axial direction at an interval.

* * * * *